Nov. 26, 1935. C. D. TANNER Plant Pat. 151
ROSE
Filed May 31, 1935
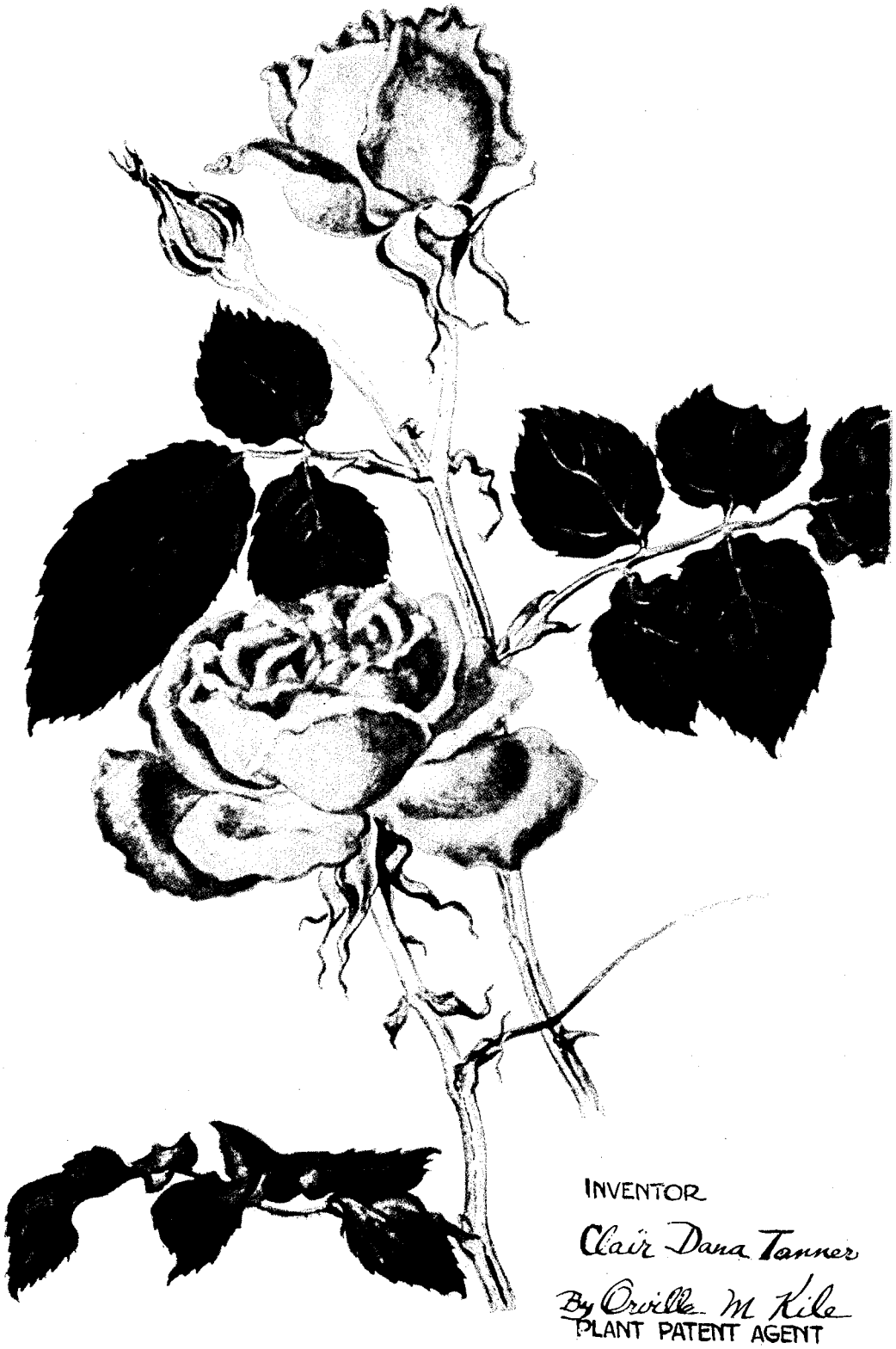
INVENTOR
Clair Dana Tanner
By Orville M Kile
PLANT PATENT AGENT Patented Nov. 26, 1935

Plant Pat. 151

UNITED STATES PATENT OFFICE

151

ROSE

Clair Dana Tanner, Holland, N. Y.

Application May 31, 1935, Serial No. 24,414

1 Claim. (Cl. 47—61)

My present invention relates to an improvement in hybrid tea roses whereby a predominantly white stem is produced which, contrasted with the deep green of the foliage, gives a novel and pleasing effect.

My new variety is a sport of the well known variety Templar. I first discovered this sport in March, 1932, and have since reproduced it from cuttings, in quantity, and have thoroughly tested it under different conditions of soil, moisture, temperature and other growing factors. These tests prove that the white stems are an inherent character and in no way the result of growing conditions. The vigorous growth and profuse foliage of this variety eliminate any question of disease as the cause of the white stems.

The accompanying illustrations show in full color, and as nearly natural as possible, two flowers and a tight bud, together with foliage and stems, of this new variety taken from a greenhouse in late April and cut about three days.

The following is a detailed description of plant and flower under conditions herein set forth:

*The plant.*—Attains a size similar to that of Templar or Briarcliff. In greenhouse use it is a strong grower and a good producer. It has not been grown out-of-doors.

*Foliage.*—Profuse. The leaves are large and numerous, relatively broad for their length although not rounded; short spaces between branches make heavy foliage near flower; moderately deep and numerous serrations on edges of leaves. Forest green (Plate XVII, Ridgway's Color Standards) or slightly darker in color; semi-glossy.

*Stipules.*—Medium broad with pointed tips.

*Thorns.*—From the flower downward to the fourth or fifth leaf no thorns appear. The stem is entirely smooth or with only an occasional hair. Below the fourth leaf there may be an occasional thorn, pink in color and downward curving. The rachises of the leaves below the third usually bear one or two small thorns on the lower side.

*Stems.*—Rather stout and either white or pinkish in color. On some stems the color is almost entirely white while others have a distinctly pinkish tint. The degree of whiteness is greatest nearest the flower, the hips being almost entirely white on the opened flower. Below the first leaf a single line or streak of green is found; below the second leaf a second green streak appears and as the third and fourth leaves are passed other green streaks appear. Thus at a distance of eight to twelve inches below the flower the stem becomes predominantly green and of course the lower part of the bush is entirely green.

*Hips.*—White with a greenish tint in the bud. On most of the mature flowers the hips are white with little or no green tint. Round rather than tapered.

*Sepals.*—Broad and of medium length, not foliaceous, characterized by a white streak up the middle of each sepal, the streak being broad at the base and tapering to a point. In some cases the white areas are slightly streaked with green.

*Flowers.*—The flowers resemble Templar in color but are heavier, somewhat larger, and have more petals. Greenhouse specimens in late April in western New York average about 24 large petals and 8 smaller central petals. Petals are cordate in shape and a number of them have a white streak down the center showing only on the inside surface of the petal; all have a small white to yellowish area on the inner surface at the point of attachment.

The color, which is approximately Carmine (Ridgway's Color Standards and Nomenclature, Plate I), is rather uniform, but the white radiates out somewhat from the point of attachment. The petals are velvety on the inside and considerably darker than on the outside.

This variety is quite fragrant.

*Stamens and pistils.*—Quite numerous and large, pinkish in color with brown anthers. Many pistils, pink in color and with white tops. These numerous sex organs form considerable bulk which tends to make a larger flower.

Having thus disclosed my invention, I claim,

The variety of rose herein described and illustrated, characterized particularly by its white and pinkish-white stems.

CLAIR DANA TANNER.